US012571809B2

(12) United States Patent
Bourdat et al.

(10) Patent No.: US 12,571,809 B2
(45) Date of Patent: Mar. 10, 2026

(54) AUTOMATED SYSTEM FOR PREPARING A BIOLOGICAL SAMPLE

(71) Applicant: Commissariat à l'Energie Atomique et aux Energies Alternatives, Paris (FR)

(72) Inventors: Anne-Gaëlle Bourdat, Grenoble (FR); Mélissa Baque, Grenoble (FR); Thomas Bordy, Grenoble (FR)

(73) Assignee: Commissariat à l'Energie Atomique et aux Energies Alternatives, Paris (FR)

( * ) Notice: Subject to any disclaimer, the term of this patent is extended or adjusted under 35 U.S.C. 154(b) by 669 days.

(21) Appl. No.: 18/061,129

(22) Filed: Dec. 2, 2022

(65) Prior Publication Data

US 2023/0176081 A1 Jun. 8, 2023

(30) Foreign Application Priority Data

Dec. 3, 2021 (FR) ...................................... 21 12885

(51) Int. Cl.
*G01N 35/00* (2006.01)
*B01L 3/00* (2006.01)
(Continued)

(52) U.S. Cl.
CPC .. *G01N 35/00584* (2013.01); *B01L 3/502715* (2013.01); *C12M 35/04* (2013.01);
(Continued)

(58) Field of Classification Search
None
See application file for complete search history.

(56) References Cited

U.S. PATENT DOCUMENTS

| | | | |
|---|---|---|---|
| 10,160,947 B2 | 12/2018 | Bourdat et al. | |
| 2004/0053334 A1* | 3/2004 | Ratner | C12M 25/06 |
| | | | 435/7.1 |

(Continued)

FOREIGN PATENT DOCUMENTS

| | | | |
|---|---|---|---|
| WO | WO 2015/181743 A1 | 12/2015 | |
| WO | WO-2018125832 A1 * | 7/2018 | B01L 3/50857 |

OTHER PUBLICATIONS

Riba, J., Schoendube, J., Zimmermann, S. et al. Single-cell dispensing and 'real-time' cell classification using convolutional neural networks for higher efficiency in single-cell cloning. Sci Rep 10, 1193 (2020). (Year: 2020).*

(Continued)

*Primary Examiner* — Neil N Turk
*Assistant Examiner* — Benjamin Joseph Kass
(74) *Attorney, Agent, or Firm* — Oblon, McClelland, Maier & Neustadt, L.L.P.

(57) ABSTRACT

An automated system for preparing a biological sample containing biological species, and including a support plate wherein one or more through-wells are made, each through-well having two opposite accesses, a first access and a second access, the first access being separated from the second access by a filter-forming porous wall against which the biological sample that is to undergo lysis may be placed, and, for each well: a first mobile member, that can be actuated to move translationally along the axis of the well so as to become inserted across the first access thereof, a second mobile member, that can be actuated to move translationally along the axis of the well so as to become inserted across the second access thereof, stimulation means of mechanical and/or thermal type for stimulating each first mobile member and/or each second mobile member and/or the support plate.

10 Claims, 3 Drawing Sheets

(51) Int. Cl.

| | |
|---|---|
| *C12M 1/34* | (2006.01) |
| *C12M 1/42* | (2006.01) |
| *G01N 35/02* | (2006.01) |
| *G01N 35/04* | (2006.01) |
| *G01N 35/10* | (2006.01) |

(52) U.S. Cl.
CPC ............. *C12M 41/40* (2013.01); *G01N 35/02* (2013.01); *G01N 35/1074* (2013.01); *B01L 2200/025* (2013.01); *B01L 2300/042* (2013.01); *B01L 2300/0681* (2013.01); *B01L 2300/0858* (2013.01); *B01L 2300/0861* (2013.01); *G01N 2035/00346* (2013.01); *G01N 2035/0415* (2013.01); *G01N 2035/0418* (2013.01); *G01N 2035/046* (2013.01)

(56) References Cited

U.S. PATENT DOCUMENTS

| | | | |
|---|---|---|---|
| 2013/0164754 A1 | 6/2013 | Malik et al. | |
| 2013/0217113 A1* | 8/2013 | Srinivasan | ............. C12N 1/066 435/306.1 |
| 2014/0087359 A1 | 3/2014 | Njoroge et al. | |
| 2015/0024481 A1 | 1/2015 | Malik et al. | |
| 2017/0218326 A1 | 8/2017 | Bourdat et al. | |
| 2021/0179997 A1* | 6/2021 | Li | ......................... C12M 41/46 |
| 2021/0346885 A1 | 11/2021 | Govyadinov et al. | |

OTHER PUBLICATIONS

Ahmed, D., Ozcelik, A., Bojanala, N. et al. Rotational manipulation of single cells and organisms using acoustic waves. Nat Commun 7, 11085 (2016). (Year: 2016).*

Conrad D. James, Paul C. Galambos, Murat Okandan, Susan Brozik, Monica Manginell, Andreas Acrivos, Dawn J. Bennett, Boris Khusid, Microsystem Strategies for Sample Preparation in Biological Detection, Sandia National Laboratories, (2004). (Year: 2004).*

French Preliminary Search Report and Written Opinion Issued Jul. 18, 2022 in French Application 21 12885 filed on Dec. 3, 2021 (with English Translation of Categories of Cited Documents), 11 pages.

* cited by examiner

AUTOMATED SYSTEM FOR PREPARING A BIOLOGICAL SAMPLE

TECHNICAL FIELD OF THE INVENTION

The present invention relates to an automated system for preparing a biological sample.

PRIOR ART

The preparation of a biological sample often incorporates a step of lysis of the biological species present in the sample. Biological-cell lysis is often needed in order to collect and study intra-cellular material, for example cell DNA.

The methods conventionally used for the lysis of biological species are as follows:

Chemical lysis which consists in adding a chemical lysis solution to the biological species in order to burst the cells;

Thermal shock (freeze-thaw) lysis which consists in putting the biological species through a temperature cycle;

Electric field (sonication) lysis which consists in subjecting the biological species to an electric field;

Mechanical lysis which consists in grinding the biological species to release the biological material.

Various mechanical lysis solutions have already been proposed in the prior art, notably in patent applications WO2015/181743A1 and EP3222989A1. These solutions consist mainly in grinding the biological species against a rough wall, or using high-shear mixing.

These earlier solutions are not, however, suitable for performing lysis on biological samples at a high rate and possibly with a number of samples in parallel.

It is an objective of the invention to propose a system capable of preparing biological samples at a high rate, and that is potentially capable of processing a plurality of samples in parallel.

SUMMARY OF THE INVENTION

This objective is achieved by an automated system for preparing a biological sample containing biological species, and comprising:

a support plate in which one or more through-wells are made, each through-well having two opposite accesses, a first access and a second access, the first access being separated from the second access by a filter-forming porous wall against which said biological sample that is to undergo lysis may be placed, and, for each well:

a first mobile member, that can be actuated to move translationally along the axis of the well so as to become inserted across the first access thereof, a second mobile member, that can be actuated to move translationally along the axis of the well so as to become inserted across the second access thereof, drive means driving the translational movement of each first mobile member and of each second mobile member, stimulation means of mechanical and/or thermal type for stimulating each first mobile member and/or each second mobile member and/or the support plate, a control unit, configured to:

command said drive means, command said stimulation means.

According to one particular feature, the drive means are configured to move said support plate between at least two distinct positions: a storage position in which it is on standby awaiting use and a working position in which it is positioned to receive a biological sample in each well.

According to another particular feature, the system comprises, for each well of the support plate, means for dispensing a biological sample into each well of the support plate, the drive means being configured to move the dispensing means between two distinct positions: a storage position and a working position in which they can be controlled such that they inject a biological sample into each well.

According to another particular feature, the mechanical-type stimulation means comprise actuating means of vibratory type collaborating with the first mobile member and/or the second mobile member.

According to another particular feature, the mechanical-type stimulation means comprise actuating means causing the first mobile member and/or the second mobile member to rotate about its axis.

According to another particular feature, the thermal-type stimulation means comprise a heating element incorporated into the first mobile member and/or the second mobile member.

According to another particular feature, the first mobile member and/or the second mobile member has a free end and the system comprises, for the first mobile member and/or the second mobile member, a protective cap arranged over the free end thereof.

According to another particular feature, the system comprises a module combining a plurality of protective caps.

According to another particular feature, the system comprises, for each through-well, an elution device comprising a reservoir intended to receive an elution fluid that is to be injected into each well, and a receptacle intended to recover said elution fluid, passing through the porous wall of the well.

The invention also relates to a method for preparing a biological sample containing biological species, implemented using an automated system such as defined hereinabove, the method comprising the steps of:

commanding the drive means to position the support plate in a working position, commanding the drive means to insert the first mobile member translationally into each well across the first access thereof until it comes to bear against said porous wall, commanding the drive means to insert the second mobile member translationally into each well across the second access thereof until it comes to bear against said porous wall, commanding the mechanical-type and/or thermal-type stimulation means of the first mobile member and/or second mobile member associated with each well and/or of the support plate to bring about lysis of the biological species.

BRIEF DESCRIPTION OF THE FIGURES

Other features and advantages will become apparent from the following detailed description, which is given with reference to the appended drawings, in which.

DETAILED DESCRIPTION OF AT LEAST ONE EMBODIMENT

In the rest of the description, the terms "top", "bottom", "upper" and "lower" are to be understood with reference to an axis (A) drawn vertically on the attached figures.

The invention targets an automated system for bringing about mechanical lysis of a biological sample at a high rate, and even for bringing about a plurality of lysis operations simultaneously on a plurality of samples in parallel.

The system takes, for example, the form of a biological-sample lysis apparatus that is able to operate fully autonomously.

The system comprises a control unit UC tasked with controlling various modules (see below) of the system in order to implement the various steps of the method of the invention.

The control unit may comprise a programmable controller provided with a central processing unit module and with a plurality of input/output modules.

The system of the invention comprises a support plate M0.

In the apparatus, the support plate M0 is advantageously positioned horizontally.

The support plate M0 comprises one or a plurality of through-wells 10 made through its thickness. In the attached figures, the support plate M0 comprises a plurality of wells but it must be appreciated that the principle of the invention applies also to a single well in the plate.

Each well 10 in the plate M0 comprises a first access, referred to as upper access, and a second access, referred to as lower access.

Between its upper access and its lower access, a well 10 has a filter-forming porous transverse wall 100 between its upper part and its lower part.

The wall 100 may have a smooth surface or a rough surface on the upper side and/or on the lower side. The biological species Y that are to undergo lysis are placed against the rough wall, to facilitate and accelerate the grinding of the biological species therein.

Figure 1:
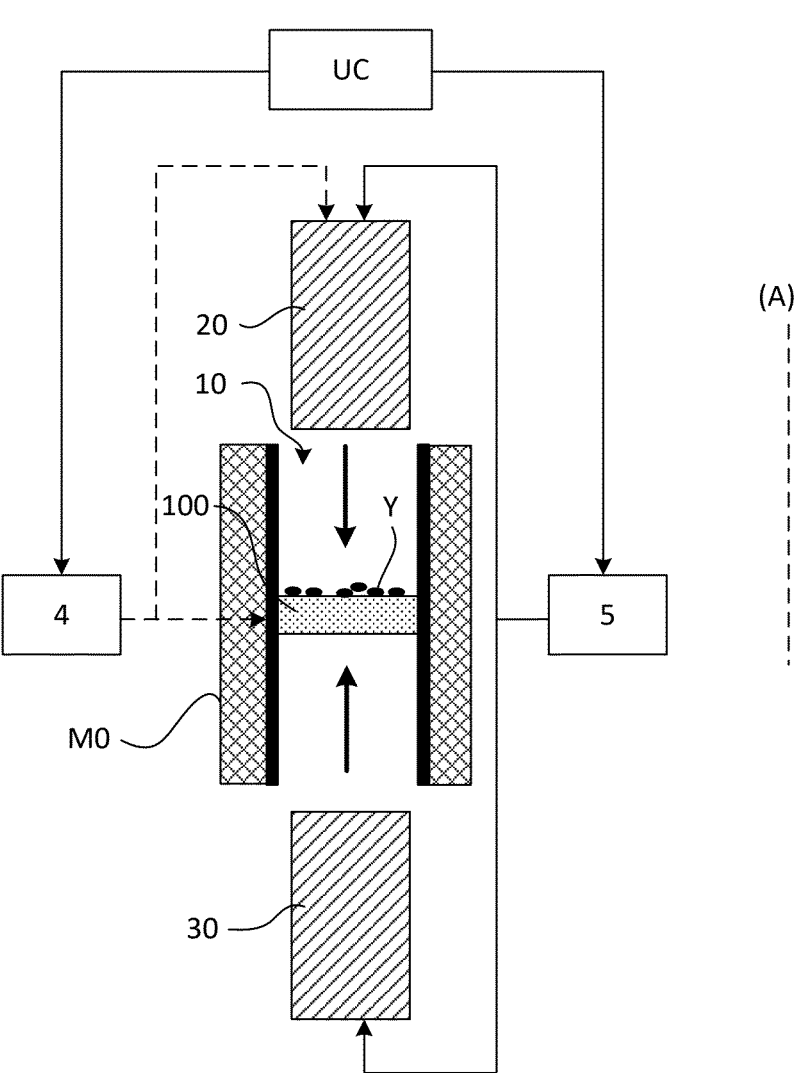
FIG. 1 shows the simplified architecture of the system of the invention.
Figure 2:
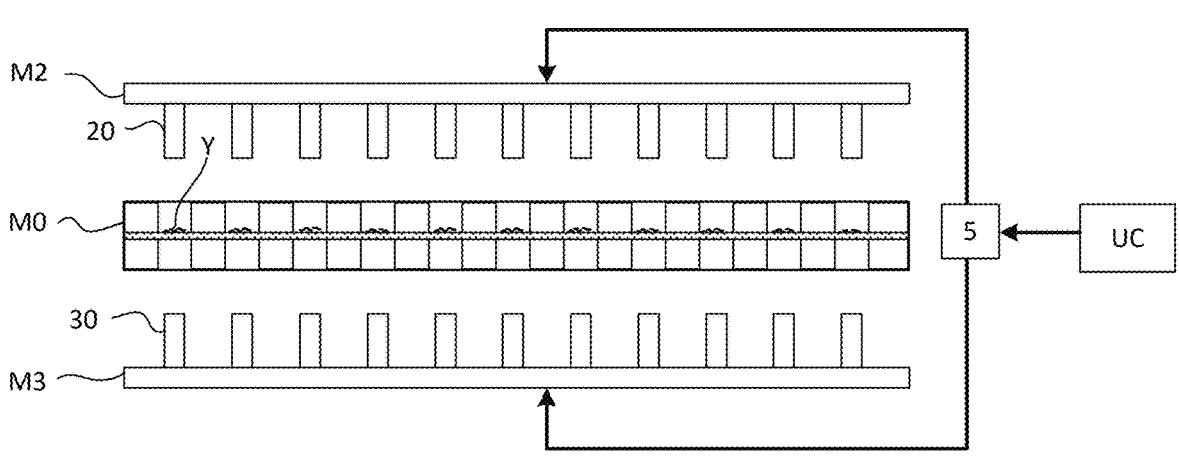
FIG. 2 depicts an improved version of the system of the invention.

With reference to FIG. 1, for each well 10 of the support plate M0, the system comprises:

a first mobile member 20, that can be actuated to move translationally along the axis of the well 10 so as to become inserted across the upper access thereof, a second mobile member 30, that can be actuated to move translationally along the axis of the well so as to become inserted across the lower access thereof, mechanical and/or thermal stimulation means 4 for stimulating the first mobile member and/or the second mobile member and/or the support plate M0.

The system also comprises drive means 5, commanded by the control unit UC. These drive means 5 may comprise motors, arms, actuating cylinders or the equivalent, capable of moving the modules and the like of the system along various axes and in various planes.

The drive means 5 of the system are notably configured and arranged in such a way as to:

move the first mobile member 20 and the second mobile member 30 in translational movements (see below), move and reinstate the support plate M0, move each module of the system, according to the method step being implemented.

Indeed it should be noted that the system may comprise a plurality of support plates M0, which for example are all identical, present in a storage space and on standby waiting to be brought into the working position. The control unit UC is tasked with selecting a support plate from among the collection of support plates available in the storage space and with commanding drive means 5 in order to cause the selected support plate to move from the storage position to the working position.

The dispensing means are intended to deliver to the well the biological sample X that is to be processed. The biological sample X may be in the form of a liquid containing biological species Y. The liquid part may be removed on passing through the porous wall of the well 10, leaving behind on the upper face of the wall 100 only the biological species Y that are to undergo lysis.

These dispensing means are optional because the support plate M0 could be supplied prefilled with a sample X to be treated already present in each well.

For all of the wells in the support plate, the dispensing means may be combined into a single dispensing module M1 comprising a plurality of reservoirs 70.

The drive means 5 are configured to place the dispensing module M1 over the support plate M0, positioning each reservoir so that it faces a distinct well 10 so as to deliver a sample X into each well.

Once the samples X have been injected into each well 10 in the support plate M0, the dispensing module M1 is withdrawn, under the command of the drive means 5.

For each well 10, the system comprises a first mobile member 20 and a second mobile member 30, these being used for the lysis of the biological species Y present in the well 10.

The first mobile member 20 is inserted translationally into the well via the upper access thereof and the second mobile member 30 is inserted translationally into the well via the lower access thereof. The transverse wall 100 of the well 10 may thus be trapped between the two mobile members.

The first mobile member 20 and the second mobile member 30 may each take the form of a rigid rod having a first end fixed to a mobile support and an opposite end which is free.

The free end of the mobile member intended to perform the lysis of the biological species may or may not be structured, in order to facilitate the grinding operation.

All of the first mobile members may be combined into a single module M2 that can be actuated for all wells in the support plate.

Likewise, all of the second mobile members may be combined into a single module M3 that can be actuated for all wells in the support plate.

The drive means 5 are configured to position each of the two modules M2, M3 such that their mobile members face a distinct well in the support plate. The drive means 5 are then configured to drive each mobile member translationally in such a way that, for each well:

the first mobile member comes to bear via its free end against the upper face of the transverse wall of the well, the second mobile member comes to bear via its free end against the lower face of the transverse wall of the well.

The two mobile members make it possible to create a solution that is mechanically stable, in which the lower mobile member acts as a support for the upper mobile member during lysis.

For each well, the system comprises stimulation means for stimulating the first mobile member and/or the second mobile member and/or the support plate M0. These stimulation means are intended to allow the lysis of the biological species present in the biological sample.

Nonlimitingly, the stimulation means 4 may be of mechanical and/or thermal type.

The mechanical stimulation means 4 may be of vibratory type. In that case, vibration may be applied to the mobile member intended to be in contact with the biological species Y that are to undergo lysis. It is also possible to hold the two mobile members in a fixed position and cause the support plate to vibrate.

Thus, at least one mobile member and/or the support plate M0 is/are actuated. It is also possible to actuate everything at the same time. It should be noted that lysis may be achieved by relative movement. The stimulation may be applied to the mobile member directly in contact with the biological species Y, or by stimulating the other mobile member, the one collaborating with the support plate M0 to cause it to move, or by stimulating the support plate relative to the two mobile members that remain fixed. It is also possible to actuate the mobile member in contact with the biological species in order to impart to it a rotational movement about a ball-joint connection of its first end.

The thermal-type stimulation means 4 consist for example in heating the free end of the mobile member that comes into contact with the biological species. The system may comprise a heating element common to the lysis module, the heat being diffused as far as the free end of each mobile member of the moving part. Each mobile member may also be equipped with an independent and controllable heating element, for example a miniature resistive heating element, or a Peltier-effect module.

In these various scenarios, in order to accelerate lysis, that face of the transverse wall 100 of the well 10 that supports the biological species Y is advantageously rough.

The system may comprise means for the elution of the biological material obtained in each well after lysis. For each well 10, these elution means may comprise an elution-liquid reservoir 80 intended to be placed above the well, and a receptacle 81 intended to receive the liquid after elution and situated beneath the well. Just as before, the system may comprise a module M4 combining a plurality of elution-liquid reservoirs into the one same structure, and a module M5 combining the receptacles. The reservoirs present in the module M4 and the receptacles present in the module M5 may be common to a plurality of wells 10 of the support plate M0. These two modules, referred to as elution modules, are capable of being positioned respectively above and beneath the support plate during the elution of the biological material. The drive means commanded by the control unit are configured to position each of the two elution modules M4, M5 in its working position. The module M4 also comprises a valve system commanded by the control unit and intended to control the release of the elution liquid stored in each reservoir of the module M4 and intended for each well of the support plate.

For each mobile member intended to come into contact with the biological species, the system may comprise a protective cap 90 to be fitted onto its free end. It is possible to provide a protective module M6, combining all of the caps 90 into a single element, and intended to be fitted onto the mobile-members support module M2 or M3. The drive means are also configured to suit this protective module M6.

Figure 3:
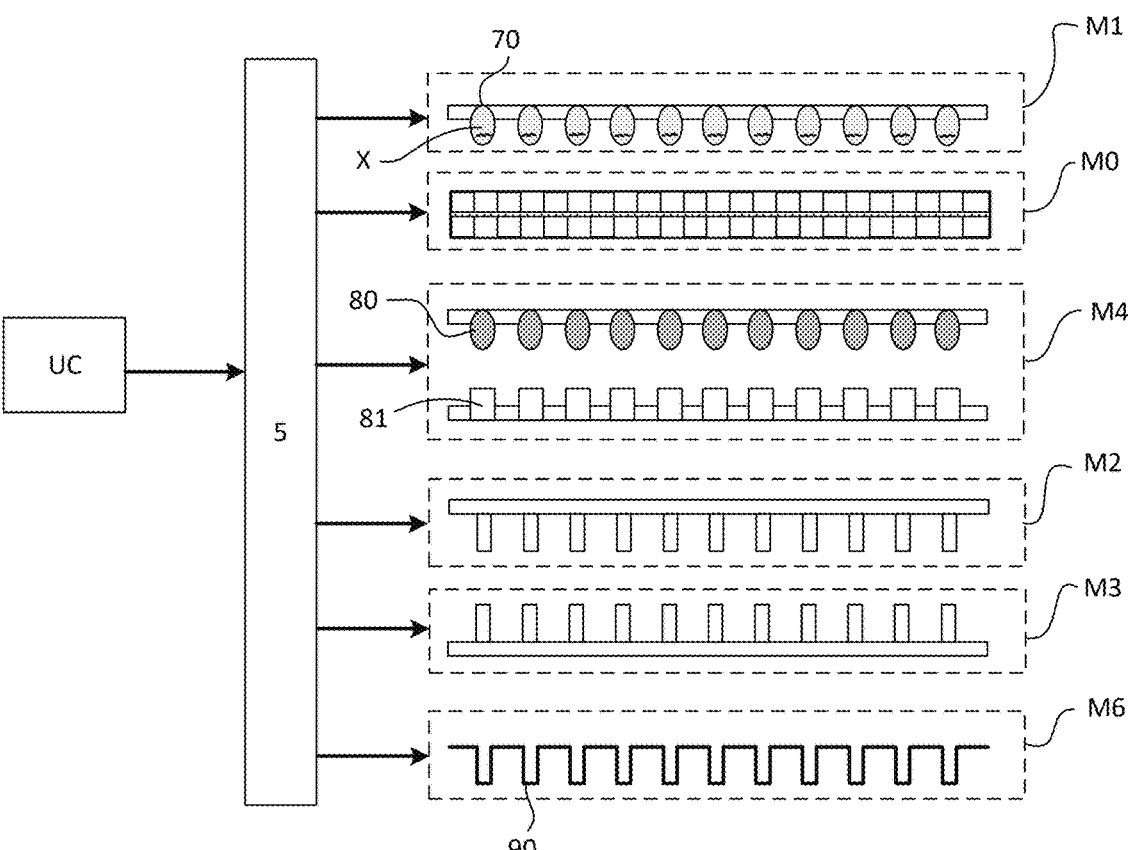
FIG. 3 shows one specific architecture of the system of the invention.

FIG. 3 schematically shows again the various modules M0 to M6 of the invention, showing that they can be actuated by the drive means 5 via commands from the control unit UC.

Figure 4:
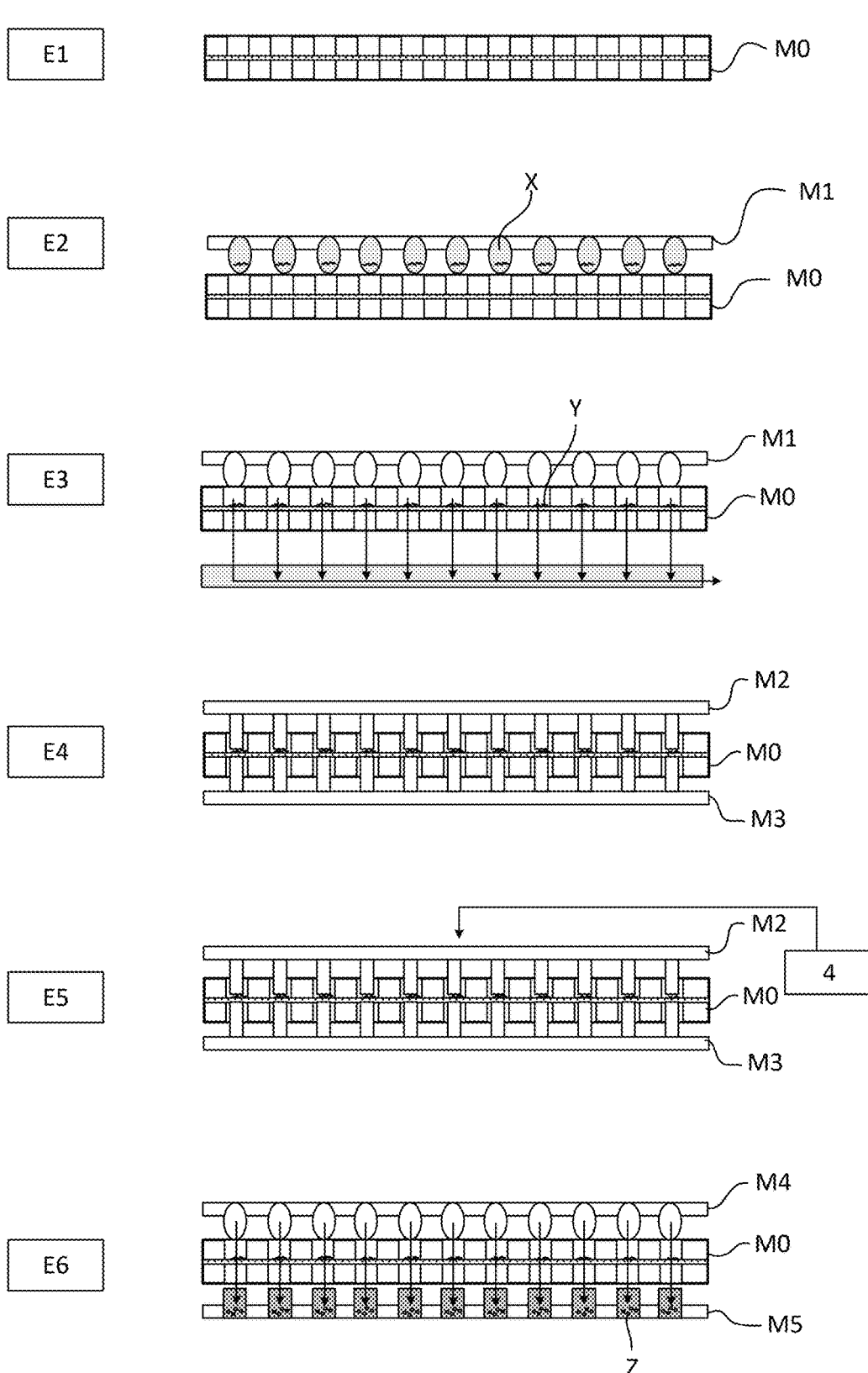
FIG. 4 illustrates the various steps of the preparation method implemented using the system according to the invention.

With reference to FIG. 4, the system may operate as follows:

E1: The control unit UC selects a support plate M0 and commands the drive means 5 to position the selected support plate in the working position, so that it is horizontal.

E2: The control unit commands the drive means 5 to position the dispensing module over the support plate.

E3: The control unit commands the dispensing module M1 to deliver a biological sample X to each well in the support plate M0 and cause it to pass through the porous wall of each well. The filtered liquid is removed.

The control unit commands the drive means 5 to withdraw the dispensing module.

The control unit commands the drive means 5 to position the lysis modules M2, M3.

E4: The control unit commands the drive means 5 to move the lysis modules M2, M3 translationally so that a first mobile member 20 is inserted into each well via the upper access thereof and so that a second mobile member 30 is inserted into each well via the lower access thereof. The two mobile members each come to bear against the two opposite faces of the transverse wall of the well.

E5: The control unit commands the stimulation means 4 to perform lysis of the biological species present in each well.

As indicated above, the stimulation may be of various types, mechanical and/or thermal, applied to one or both mobile members and/or to the support plate M0.

Once lysis is over, the control unit commands the withdrawal of the lysis modules M2, M3.

The control unit may command the elution of the biological material obtained in each well. The control unit commands the drive means to position the elution modules M4, M5 respectively above and beneath the support plate.

E6: The control unit commands the injection of an elution liquid into each well of the support plate. The liquid containing the biological material Z of interest is recovered in each receptacle of the module M5.

The system of the invention offers numerous advantages, among which:

it allows one or more samples to undergo lysis in parallel in a fully automated manner;

it uses hardware conventionally employed in the field of the handling of biological samples;

It allows lysis with no human intervention, and advantageously using single-use hardware, thereby limiting the risks of contamination.

The invention claimed is:

1. An automated system for preparing a biological sample containing biological species, wherein the automated system comprises:

a support plate wherein one or more through-wells are made, each through-well having two opposite accesses, a first access and a second access, the first access being separated from the second access by a filter-forming porous wall against which said biological sample that is to undergo lysis may be placed, and, for each well:

a first mobile member, configured to be actuated to move translationally along an axis of the well so as to become inserted across the first access thereof, a second mobile member, configured to be actuated to move translationally along the axis of the well so as to become inserted across the second access thereof, a drive means driving the translational movement of each of the first mobile member and the second mobile member, a stimulation means of mechanical and/or thermal type for stimulating each first mobile member and/or each second mobile member and/or the support plate, a control unit, configured to:

command said drive means, and command said stimulation means.

2. The system according to claim 1, wherein the drive means are configured to move said support plate between at least two distinct positions: a storage position wherein said support plate is on standby awaiting use and a working position wherein said support plate is positioned to receive a biological sample in each well.

3. The system according to claim 1, comprising, for each well of the support plate, a dispensing module that dispenses a biological sample into each well of the support plate, the drive means being configured to move the dispensing module between two distinct positions: a storage position and a working position wherein the dispensing module can be controlled such that the dispensing module injects a biological sample into each well.

4. The system according to claim 1, wherein the stimulation means is the mechanical-type stimulation means, wherein the mechanical-type stimulation means comprises actuating means of vibratory type collaborating with the first mobile member and/or the second mobile member.

5. The system according to claim 1, wherein the mechanical-type stimulation means comprise actuating means causing the first mobile member and/or the second mobile member to rotate about its axis.

6. The system according to claim 1, wherein the stimulation means is the thermal-type stimulation means, wherein the thermal-type stimulation means comprises a heating element incorporated into the first mobile member and/or the second mobile member.

7. The system according to claim 1, wherein the first mobile member and/or the second mobile member has a free end and wherein the system comprises, for the first mobile member and/or the second mobile member, a protective cap arranged over the free end thereof.

8. The system according to claim 7, comprising a module which mechanically connects a plurality of protective caps in an array.

9. The system according to claim 1, comprising, for each through-well, an elution device comprising a reservoir intended to receive an elution fluid that is to be injected into each well, and a receptacle intended to recover said elution fluid, passing through the porous wall of the well.

10. A method for preparing a biological sample containing biological species, the method comprising the steps of:

providing an automated system as defined in claim 1, commanding the drive means to position the support plate in a working position, commanding the drive means to insert the first mobile member translationally into each well across the first access thereof until it comes to bear against said porous wall, commanding the drive means to insert the second mobile member translationally into each well across the second access thereof until it comes to bear against said porous wall, commanding the mechanical-type and/or thermal-type stimulation means of the first mobile member and/or second mobile member associated with each well and/or of the support plate to bring about lysis of the biological species.

\* \* \* \* \*